United States Patent [19]

Yamasaki et al.

[11] Patent Number: 5,362,418
[45] Date of Patent: Nov. 8, 1994

[54] GEL-LIKE EMULSION AND O/W EMULSION OBTAINED FROM THE GEL-LIKE EMULSION

[75] Inventors: Seiji Yamasaki, Funabashi; Toshiyuki Suzuki, Ichikawa; Chikako Hirata, Kohbe, all of Japan

[73] Assignee: Kao Corporation, Tokyo, Japan

[21] Appl. No.: 90,634

[22] Filed: Jul. 12, 1993

Related U.S. Application Data

[60] Continuation of Ser. No. 632,629, Dec. 26, 1990, abandoned, which is a division of Ser. No. 437,332, Nov. 20, 1989, abandoned, which is a continuation of Ser. No. 939,684, Dec. 9, 1986, abandoned.

[30] Foreign Application Priority Data

Dec. 23, 1985 [JP] Japan ................. 60-289800

[51] Int. Cl.$^5$ ................. B01J 13/00; B01F 17/14
[52] U.S. Cl. ................. 252/314; 252/312; 252/315.1; 514/939; 514/944; 424/401
[58] Field of Search ................. 252/312, 314, 315.1; 514/939, 944, 938; 424/401

[56] References Cited

U.S. PATENT DOCUMENTS

| | | | |
|---|---|---|---|
| 4,379,755 | 4/1983 | Yamada et al. | 252/314 X |
| 4,400,295 | 8/1983 | Ootsu et al. | 252/314 X |
| 4,536,519 | 8/1985 | Suzuki et al. | 514/785 |
| 4,704,220 | 11/1987 | Goddard et al. | 252/75 |
| 4,776,976 | 10/1988 | Nakamura et al. | 252/312 |
| 4,868,163 | 9/1989 | Takei et al. | 514/76 |
| 5,085,854 | 2/1992 | Fukuda et al. | 424/63 |

FOREIGN PATENT DOCUMENTS

2139112 11/1984 United Kingdom .

OTHER PUBLICATIONS

European Search Report dated Apr. 27, 1987.
M. S. Rosen, *Surfactants and Interfacial Phenomena*, (John Wiley & sons, N.Y., 1978) pp. 12–13.
*McCutcheon's Detergents & Emulsifiers, 1973 N. America Ed.*, McCutcheon's Division, Allured Pupbl. Corp. Ridgewood, N.J.

*Primary Examiner*—Robert L. Stoll
*Assistant Examiner*—Daniel S. Metzmaier
*Attorney, Agent, or Firm*—Oblon, Spivak, McClelland, Maier & Neustadt

[57] ABSTRACT

A gel-like emulsion is prepared by adding an oil to a surfactant continuous phase formed of a monoalkyl phosphate salt, polyhydric alcohol and water.

The gel-like emulsion is scarcely dependent on temperature, and a fine and uniform O/W emulsion prepared from the gel-like emulsion reveals excellent stability at the time of production and at storage. The gel-like emulsion contains only a small amount of alkyl phosphate surface active agent of low irritativeness, so that it is usable for cosmetics, pharmaceuticals, industrial products and the like, which are required to have low irritation and high safety.

16 Claims, No Drawings

GEL-LIKE EMULSION AND O/W EMULSION OBTAINED FROM THE GEL-LIKE EMULSION

This application is a continuation of application Ser. No. 07/632,629, filed on Dec. 26, 1990, which was a division of application Ser. No. 07/437,332, filed on Nov. 20, 1989, which was a continuation of application Ser. No. 06/939,684, filed on Dec. 9, 1986, all now abandoned.

BACKGROUND OF THE INVENTION

1) Field of the Invention

This invention relates to a gel-like emulsion comprising a surface active agent phase as a continuous phase. More particularly, the invention relates to a gel-like emulsion which can readily yield O/W emulsion of high quality by addition of an aqueous phase and to the thus obtained O/W emulsion.

2) Description of the Prior Art

Emulsification methods for obtaining a fine, uniform emulsion generally include a phase inversion emulsification method using nonionic or ionic surface active agents and a gel emulsification method using nonionic surface active agents.

According to the phase inversion emulsification method, a surface active agent is dissolved or dispersed in oil, followed by addition of water phase to the system. As water phase is added, the system is inversed from a W/O state to an O/W state. Through this phase inversion, a fine and uniform emulsion is obtained.

However, there is a limit to an amount of the oil which can be emulsified by a certain amount of surface active agent, and relatively a large amount of surface active agent is required to obtain an emulsion consisting of fine particles. Further, in order to obtain an emulsion in a proper state, it is necessary to adjust a hydrophilic lipophobic balance (HLB) of the surfactant system depending upon a type of oil to be emulsified. In addition, since a particle size of emulsion depends largely on mechanical shear which is imposed to the system during the emulsification, there are some cumbersome problems for determining conditions for the emulsion preparation.

According to the gel emulsification method using nonionic surface active agents, O/W emulsions are obtained by dissolving a nonionic surface active agent in a water-soluble solvent with or without addition of an aqueous phase to give a continuous surface active agent phase, gradually adding an oil to the continuous phase to obtain a gel-like emulsion, and further adding water to the gel-like emulsion. A fine and uniform emulsion can be obtained by this method, however it is necessary to select a proper nonionic surface active agent suitable for the oil to be emulsified. Since H/L balance of a nonionic surface active agent is much affected by temperature, the state of emulsion also depends upon the emulsification temperature. Therefore, in preparing and preserving the above described gel-like emulsion, as well as in producing an O/W emulsion by using the gel-like emulsion and preserving it, temperature is one of very important factors with regard to the emulsion stability. For instance, there is a case where even if a gel-like emulsion can be formed at a low temperature, it cannot be formed at a higher temperature, or an O/W emulsion prepared by a gel-like emulsion is unstable at a high temperature. The gel emulsification method using nonionic surface active agent thus involves such disadvantages on production and quality of emulsion.

SUMMARY OF THE INVENTION

The present inventors made studies on an emulsification method using ionic surface active agents in order to overcome these disadvantages of the prior art methods and to obtain a fine and uniform O/W emulsion. As a result, it was found that monoalkyl phosphate monosalts are capable of forming gels along with polyhydric alcohols, water and oils, that when an aqueous phase is added to the gel, fine and stable O/W emulsions can be obtained, and further that this process of emulsification and the stability of the formed emulsion are hardly affected by the temperature.

More particularly, the present invention provides a gel-like emulsion which is prepared by adding and mixing an oil to a surface active agent phase formed of a monoalkyl phosphate salt of the following general formula (I), a polyhydric alcohol and water

in which R represents a hydrocarbon group having from 12 to 24 carbon atoms and X represents an alkali metal, a basic amino acid or an organic base, and also provides an O/W emulsion obtained by adding an aqueous phase to the gel-like emulsion and mixing them.

DETAILED DESCRIPTION OF THE INVENTION AND PREFERRED EMBODIMENTS

The gel-like emulsion according to the invention is produced by preparing a surface active agent phase from the monoalkyl phosphate salt (I), a polyhydric alcohol and water, adding an oil to the continuous phase, and mixing them. More particularly, an aqueous polyhydric alcohol solution having a content of a polyhydric alcohol of not less than 60%, preferably not less than 80%, is used to dissolve 0.1 to 60%, preferably from 0.5 to 5%, of a monoalkyl phosphate salt (I) on the weight basis of the aqueous solution to prepare the surface active agent phase. An oil is further added and mixed in amounts of from 10 to 75%, preferably from 20 to 50%, on the weight basis of the surface active agent phase to obtain an O/D (oil in surface active agent phase) transparent or semitransparent gel-like emulsion.

By employing the emulsification method of the present invention, the gel-like emulsion can be prepared at a wide range of temperatures. This is a notable difference between the present method and a conventional gel emulsification method using nonionic surface active agent. The transparent or semitransparent gel-like emulsion having good property can be obtained by emulsifying at from room temperature to 80° C., in general, according to the inventive method.

The water for the preparation of the gel-like emulsion should be added in an amount of from 5 to 20% of the composition.

The monoalkyl phosphate salts of the formula (I) used in the present invention are known compounds. These salts may be prepared by neutralizing a monoalkyl phosphoric acid with a basic substance in a separate system and formulated in an emulsion system, or the acid and the basic substance may be separately added to the emulsion system. When monoalkyl phosphoric acids are neutralized with basic substances, it is not necessarily to completely neutralize the acid, but partial neutralization is sufficient. Moreover, basic substances may be present in excess over an amount necessary for the neutralization. The amount of a basic substance is so selected as to control the pH of an intended emulsion. The basic substance is generally used in an amount of from 0.2 to 1.8 mols, preferably from 0.4 to 1.0 mol, with respect to the monoalkyl phosphoric acid. Examples of the monoalkyl phosphate salts (I) are those of the formula (I) in which R represents an alkyl group having from 10 to 24, preferably from 12 to 18, carbon atoms. With the carbon atoms less than 10, the odor is offensive and emulsifing ability becomes poor. With more than 24 carbon atoms, emulsifiability is low and the state of an emulsion deteriorates with time. Preferable groups include linear alkyl groups, linear alkenyl groups and branched alkyl groups shown below.

(i) Methyl-branched alkyl group of the following formula (II):

in which h is an integer of from 2 to 14 and i is an integer of from 3 to 11, provided that h+i is in the range of from 9 to 21, preferably from 11 to 19.

(ii) Beta-branched alkyl group of the following formula (III):

in which k is an integer of from 5 to 11 and l is an integer of from 3 to 10 provided that k+l is from 8 to 20, preferably from 10 to 18.

(iii) Alpha-branched alkyl group of the following formula (IV):

in which p is an integer of from 1 to 20 and q is an integer of from 1 to 20, provided that p+q is from 9 to 21, preferably from 11 to 19.

(iv) Multi-branched alkyl group of, for example, the following formula (v):

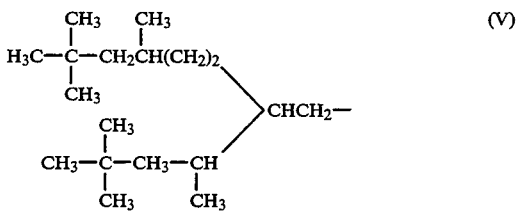

Of these branched alkyl groups, the groups (i) and (ii) are preferred. Examples of the counter ion, X, include alkali metals such as lithium, sodium, potassium and the like, basic amino acids such as arginine, ornithine, lysine, oxylysine and the like, and groups derived from alkanolamines having a hydroxyalkyl group having 2 or 3 carbon atoms such as triethanolamine, diethanolamine, monoethanolamine and the like. As linear alkyl groups, basic amino acids, particularly arginine is preferred. As branched alkyl groups, any counter ions are favorable.

The polyhydric alcohols include, for example, glycerine, ethylene glycol, diethylene glycol, triethylene glycol, hexanediol, butylene glycol, heptanediol, hexylene glycol, pentanediol, butanediol, propylene glycol, butylene glycol, dipropylene glycol (molecular weight of 60-2000), sorbitol, maltitol and the like. Preferably, trihydric or higher polyhydric alcohols such as, for example, glycerine, sorbitol and maltitol, are used.

The oils may be liquid oils and solid fats and may be substantially all oils which have been ordinarily accepted as starting materials for cosmetics. Examples of the oils include hydrocarbons, esters of higher alcohols and higher fatty acids, higher alcohols, higher fatty acids, animal and plant oils and fats, cholesterol and fatty acid esters and the like. Preferable and specific examples include liquid paraffin, solid paraffin, vaseline (petrolatum), olive oil, squalene, hydrogenated coconut oil, jojoba oil, 2-ethylhexanoic acid triglyceride, octadecyl myristate, isostearyl cholesteryl ester, silicone oil and the like. These oils may be used singly or in combination.

The thus obtained gel-like emulsion is so stable that it can be preserved at a wide range of temperatures from low to high. The gel-like emulsion may be conveniently prepared into a cosmetic such as a night cream, a cleansing cream and the like. Moreover, this emulsion may be used as a base of cosmetics and that of external agents. For example, a transparent or semitransparent jellylike cosmetic having high humectancy can be prepared by using a branched alkyl phosphate. Even when the above cosmetic is washed away with water, oil remaining on the skin surface or on the hair gives agreeable moistened feel.

The gel-like emulsion of the present invention may also be used as a starting material for O/W emulsions.

For the preparation of an O/W emulsion from the thus obtained gel-like emulsion, an aqueous phase is added. The amount of the water is not critical on condition that an O/W emulsion is prepared.

As is particularly described in Example 1 appearing hereinafter, the gel-like emulsion of the invention is able to emulsify an oil 350 times the quantity of the emulsion at an emulsification temperature of 40° C., thereby obtaining a fine O/W emulsion. Considering the quantity of oil emulsifyable by a phase inversion emulsification (about 20 times), this method of emulsification is capable of emulsifying a given quantity of oil using far less amount of the surface active agent. Under conditions where a greater amount of surface active agent is used, e.g., surface active agent:oil=1:3, a transparent O/W microemulsion can be obtained as will not be experienced in existing emulsion systems. In view of the above, it is possible to prepare from microemulsions to sub-micron emulsions by controlling a mixing ratio of an oil and a surface active agent irrespective of the type of oil. Upon comparison with the phase inversion emulsification, the present invention ensures emulsification using a smaller amount of a surface active agent, a phosphate which is inherently less irritative, so that the resultant emulsion is less irritative and has high safety.

As will be seen in Example 2 appearing hereinafter, a fine and homogeneous O/W emulsion having high stability for preservation under a wide range of temperatures can be obtained from the gel-like emulsion of the invention when an emulsification temperature is changed between 20° C. and 80° C., giving evidence that the emulsion of the invention has better temperature-independent properties than emulsions using known nonionic surface active agents.

In the emulsification method of the present invention, not only a monoalkyl phosphate salt but also other surface active agents such as monoglyceride, polyoxyethylene added type nonionic surface active agent and the like, and auxiliary surface active agents may be co-employed as a surface active ingredient.

These agents are preferably added when preparing the gel-like emulsion together with a monoalkyl phosphate salt. They may also be added when producing an O/W emulsion by adding an aqueous phase to the gel-like emulsion.

Even when these surface active agents or auxiliary surface active agents are co-employed, reselection of a main surface active agent considering HLB of the whole emulsion system is not needed, and an excellent emulsion equal to the one which is obtained by sole use of monoalkyl phosphate salt can be obtained.

The co-use of surface active agents and auxiliary surface active agents may bring about various additional effects. For instance, natural phospholipid such as lecitine (in view of odor and feel on use, hydrogenated one is preferable) is added together with a humectant when a moistening cream is produced. By so doing humecancy of the moistening cream can be retained for quite a long time.

The O/W emulsions of the present invention can be applied to creams such as a moisture cream, massage cream and the like, skin cosmetics such as a milky emulsion and the like, and also utilized as a base for make up cosmetics, hair cosmetics and external agents for the skin.

Besides the above described surface active agents and auxiliary surface active agents, thickeners such as natural and synthetic water-soluble polymers, pharmaceuticals such as an antiphlogistic agent, a blood circulation promoting agent, a trauma curing agent, a skin massage agent and the like, humectants such as an NMF factor, ordinary ingredients such as perfume, colorant, preservative and the like may be added to obtain cosmetic compositions and external agents for the skin.

The properties of the gel-like emulsion of the invention are considered to result from physical properties of monoalkyl phosphate salts. Ionic surface active agents have generally poor solubility to polyhydric alcohols, but monoalkyl phosphate salts used in the present invention are readily soluble in polyhydric alcohols forming a molecular association. Presumably, this is why emulsions of good quality are formed.

The transparent or semitransparent gel-like emulsion of the present invention is scarcely dependent on temperature, and a fine and uniform O/W emulsion prepared from the gel-like emulsion reveals excellent stability at the time of production and at storage. The gel-like emulsion contains only a small amount of alkyl phosphate surface active agent of low irritativeness, so that it is usable for cosmetics, pharmaceuticals, industrial products and the like, which are required to have low irritation and high safety.

According to the emulsification method of the present invention, it is not necessary to determine a surface active agent system having a suitable HLB for each type of oils to be emulsified. A wide variety of oils can be emulsified by a monoalkyl phosphate surface active agent. The emulsification method of the present invention is thus advantageous compared with the conventional emulsification method.

The present invention is more particularly described by way of examples.

EXAMPLE 1

Gel-like emulsions were prepared according to the formulations shown in Table 1 at 30° C. and 70° C., respectively. Ingredients (i), (iii) (iv) were mixed and homogenized. To this homogenized system, oily ingredient (ii) was added and mixed.

As shown in Table 1, transparent or semitransparent gel-like emulsions were obtained when a monoalkyl phosphate salt was used. However, gel-like emulsions were not obtained when prepared at 30° C. by using calcium stearate and at 70° C. by using POE(20) hexadecyl ether.

In Table 1:
○: a transparent or semitransparent gel was formed
Δ: A semitransparent or white gel was formed
X: no gel was formed Storage stability of the above obtained gel-like emulsions was examined. The gel-like emulsions obtained at 30° C., exceptionally emulsion D obtained at 70° C., were preserved for one week at some different temperatures. The results are shown in Table 2.

While the inventive gel-like emulsions A, B and C were stable at any temperatures, gel-like emulsions D and E were unstable and they were crystalized, separated or became cloudy.

TABLE 1

| | A | B | C | D | E | (%) F |
|---|---|---|---|---|---|---|
| Ingredients (i) | | | | | | |
| Mono-2-hexyldecyl phosphate L-arginine salt | 0.5 | — | — | — | — | 0.5 |
| Monocetyl phosphate L-arginine salt | — | 0.5 | — | — | — | — |
| Mono-2-hexyldecyl phosphate potassium salt | — | — | 0.5 | — | — | — |
| Potassium stearate | — | — | — | 0.5 | — | — |
| POE(20) hexadecyl ether | — | — | — | — | 0.5 | — |
| Ingredient (ii) 2-Ethylhexanoic acid triglyceride | 85.0 | 85.0 | 85.0 | 85.0 | 85.0 | 85.0 |
| Ingredient (iii) Glycerine | 9.5 | 9.5 | 9.5 | 9.5 | 9.5 | — |
| Ingredient (iv) Purified water | 5.0 | 5.0 | 5.0 | 5.0 | 5.0 | 14.5 |
| Formation of gel | | | | | | |
| prepared at 30° C. | ○ | ○ | ○ | X | ○ | X |
| prepared at 70° C. | ○ | ○ | ○ | Δ | X | X |

TABLE 2

| | A | B | C | D | E | F |
|---|---|---|---|---|---|---|
| Storage Temperature | | | | | | |
| −5° C. | ○ | ○ | ○ | c | ○ | — |
| 20° C. | ○ | ○ | ○ | c | ○ | — |
| Room temp. | ○ | ○ | ○ | c | ○ | — |

TABLE 2-continued

|        | A | B | C | D | E  | F |
|--------|---|---|---|---|----|---|
| 40° C. | ○ | ○ | ○ | s | op | — |
| 50° C. | ○ | ○ | ○ | s | s  | — |

In the table:
○: not changed
c: crystalized
s: separated
op: opaque

EXAMPLE 2

O/W emulsions were prepared from the gel-like emulsions according to the formulations shown in the following table and the procedure described below. An average particle size, appearance and stability of the obtained O/W emulsions are shown in Table 3.

(Formulation) (%)

|   | G | H | I | J | K | L |
|---|---|---|---|---|---|---|
| (1) Monomyristyl phosphate L-arginine salt | 10.0 | 2.0 | 0.5 | 0.085 | — | — |
| (2) Mono-2-hexyl-decyl phosphate L-arginine salt | — | — | — | — | 2.0 | — |
| (3) POE(20) octyl-dodecyl ether | — | — | — | — | — | 2.0 |
| (4) Glycerine (86% aq. sol'n) | 30.0 | → | → | → | → | → |
| (5) Hardened palm oil (mp = 40° C.) | 5.0 | → | → | → | → | → |
| (6) Squalane | 10.0 | → | → | → | → | → |
| (7) Octyldodecyl myristate | 15.0 | → | → | → | → | → |
| (8) Purified water | 30.0 | 38.0 | 39.5 | 39.915 | 38.0 | 38.0 |

(Preparation)

Ingredients (1) to (4) were mixed and homogenized. Oily ingredients (5) to (7) preliminary mixed under heating were added to the above obtained gel at 40° C. To the resultant system, purified water (ingredient (8)) was added under stirring, thereby obtaining an O/W emulsion.

TABLE 3

|   | G | H | I | J | K | L |
|---|---|---|---|---|---|---|
| Average particle size (nm) | 50 | 80 | 110 | 265 | 70 | >1000 |
| Appearance | pale blue transparent | slightly white semitransparent | slightly white-white | white | slightly white semitransparent | white |
| Amount of emusified oil (emusified oil/surface active agent) | 3 | 15 | 60 | 350 | 15 | 15 |
| Storage Temp. | | | | | | |
| −5° C. | ○ | ○ | ○ | ○ | ○ | separated |
| 20° C. | ○ | ○ | ○ | ○ | ○ | separated |
| room temp. | ○ | ○ | ○ | ○ | ○ | separated |
| 40° C. | ○ | ○ | ○ | ○ | ○ | separated |
| 50° C. | ○ | ○ | ○ | ○ | ○ | separated |

1) Average particle size was determined by laser-ray scattering method by using Coulter Submicron Analyser.
2) Storage stability was visually evaluated after one week storage. In the table "○" means "no changed".

EXAMPLE 3

Gel-like emulsions were prepared using the following compositions by a method described below. Water was subsequently added to each gel-like emulsion at 40° C. in an amount sufficient to bring the total amount of 100 parts by weight, thereby obtaining an O/W emulsion. The particle size was measured according to a laser-ray scattering method using a Coulter Submicron analyser. The results are shown in Table 4.

(Composition)

|   | A | B | C | D |
|---|---|---|---|---|
| (1) monomyristyl phosphate L-arginine salt | 10 | 2 | 0.5 | 0.085 |
| (2) aqueous glycerine solution (containing 86% of glycerine) | 30 | 30 | 30 | 30 |
| (3) squalane | 10 | 10 | 10 | 10 |
| (4) triglyceride | 5 | 5 | 5 | 5 |
| (5) octyldodecyl myristate | 15 | 15 | 15 | 15 |

(parts by weight)

(Preparation)

(1) and (2) were mixed and homogenized. To the resultant gel were added oils (3)–(5) dissolved at 40° C. to obtain a gel-like emulsion.

(Results)

TABLE 4

|   | amount of emulsified oils monomyristyl phosphate L-arginine salt | particle size of O/W emulsion (nm) |
|---|---|---|
| Composition A | 3 | 50 |
| Composition B | 15 | 80 |
| Composition C | 60 | 110 |
| Composition D | 350 | 265 |

As shown in the above results, the gel-like emulsions having an average particle size of several tens nm (micro emulsion) to several hundreds nm (submicro emulsion) are obtainable by controlling an incorporation amount of a monoalkyl phosphate salt. The obtained emulsions have high storage stability. In contrast, an emulsion prepared by using POE(20) octyldodecyl ether consists of particles having a diameter of one micron or more, and its storage stability is quite poor.

EXAMPLE 4

A gel-like emulsion was prepared using the following composition and manner of preparation and was emulsified with 39.5 parts by weight of water at a temperature ranging from 20° to 80° C., thereby obtaining O/W emulsions. The particle size of these emulsions was measured in the same manner as in Example 1. The results are shown in Table 2.

| (Composition) | (parts by weight) |
|---|---|
| (1) monomyristyl phosphate arginine salt | 0.5 |
| (2) aqueous glycerine solution (glycerine content of 86%) | 30 |
| (3) squalane | 10 |
| (4) triglyceride | 5 |
| (5) octyldodecyl myristate | 15 |

(Preparation)

(1) and (2) were mixed and dissolved, to which (3)–(5) were added and homogenized to obtain a gel-like emulsion.

(Results)

| Emulsification Temperature (°C.) | Particle Size of Emulsion (nm) |
|---|---|
| 20 | 100 |
| 30 | 95 |
| 40 | 90 |
| 50 | 90 |
| 60 | 105 |
| 70 | 75 |
| 80 | 80 |

As shown in the above table, emulsions having almost the same particle size can be obtained irrespective of the emulsification temperature.

EXAMPLE 5

Milky Emulsion:

A milky emulsion was prepared according to the following formulation.

| (Formulation) | |
|---|---|
| (1) monocetyl phosphate | 0.5(%) |
| (2) L-arginine | 0.25 |
| (3) aqueous glycerine solution (glycerine content of 86%) | 20.0 |
| (4) squalane | 30.0 |
| (5) isopropyl myristate | 10.0 |
| (6) fatty acid/glycerine ester | 10.0 |
| (7) preservative | suitable amount |
| (8) perfume | very small amount |
| (9) purified water | balance |

(Preparation)

(3) was dispersed in (1), to which (2) was added for neutralization, followed by uniform dissolution. To the solution was gradually added a solution of a mixture of (4)–(8) and homogenized to obtain a gel-like emulsion. Thereafter, (9) was added, thereby obtaining an O/W emulsion.

EXAMPLE 6

Cream:

A cream was prepared using the following formulation.

| (Formulation) | |
|---|---|
| (1) monocetyl phosphate | 0.5% |
| (2) L-arginine | 0.25 |
| (3) aqueous glycerine solution (glycerine content of 86%) | 10.0 |
| (4) Cetanol | 3.0 |
| (5) Stearyl alcohol | 2.0 |
| (6) fatty acid/glycerine ester | 20.0 |
| (7) squalane | 10.0 |
| (8) olive oil | 5.0 |
| (9) jojoba oil | 5.0 |
| (10) preservative | suitable amount |
| (11) perfume | very small amount |
| (12) purified water | balance |

(Preparation)

(1) was dispersed in (3), to which (2) was added for neutralization, followed by uniform dissolution. To the solution were gradually added (4)–(9) and (11) and homogenized, thereby obtaining a semitransparent gel-like emulsion. Subsequently, (10) and (12) were added to obtain an O/W emulsion.

EXAMPLE 7

Cream:

| (Formulation) | |
|---|---|
| (1) monomyristyl phosphate | 0.5% |
| (2) L-arginine | 0.25 |
| (3) aqueous glycerine solutin (glycerine content of 86%) | 15 |
| (4) stearic acid | 2 |
| (5) myristic acid | 0.2 |
| (6) squalane | 10 |
| (7) liquid paraffin | 4 |
| (8) olive oil | 5 |
| (9) octyldodecyl myristate | 5 |
| (10) paraffin | 3 |
| (11) preservative | suitable amount |
| (12) perfume | very small amount |

(Preparation)

(1) and (2) were dispersed in (3), to which (4)–(10) were added as dissolved and agitated. Thereafter, (11) and (12) were added, thereby obtaining a gel-like semitransparent cream.

EXAMPLE 8

Cream:

| (Formulation) | |
|---|---|
| (1) monomyristyl phosphate | 0.5% |
| (2) L-arginine | 0.25 |
| (3) aqueous sorbitol solution (sorbitol content of 70%) | 15 |
| (4) stearic acid | 2 |
| (5) myristic acid | 0.2 |
| (6) squalane | 10 |
| (7) liquid paraffin | 4 |
| (8) olive oil | 5 |
| (9) octyldodecyl myristate | 5 |
| (10) paraffin | 3 |
| (11) preservative | suitable amount |
| (12) perfume | very small amount |
| (13) purified water | balance |

11

(Preparation)

(1) and (2) were dispersed in (3), to which (4)–(10) were added after dissolution and well agitated, thereby obtaining a gel-like emulsion. Thereafter, (11)–(13) were added to the gel-like emulsion and agitated, thereby obtaining an O/W cream.

EXAMPLE 9

Milky Emulsion:

| (Formulation) | | |
|---|---|---|
| (1) monomyristyl phosphate | 0.5% | |
| (2) L-arginine | 0.25 | |
| (3) aqueous maltitol solution (maltitol content of 70%) | 20 | |
| (4) triglyceride | 5 | |
| (5) octyldodecyl myristate | 10 | |
| (6) squalane | 5 | |
| (7) preservative | suitable amount | |
| (8) perfume | very small amount | |
| (9) purified water | balance | |

(Preparation)

(1) and (2) were dispersed in (3), to which (4)–(6) were added after melting and homogenized to obtain a gel-like emulsion. (7)–(9) were added to the gel-like emulsion and agitated to obtain an milky emulsion.

EXAMPLE 10

Body Treatment Composition:

A body treatment composition was prepared according to the following formulation and preparation manner, and its feel on use and remaining feel were evaluated by ten female monitors and compared with those feels of commercial products. The results are shown in Table 5.

It is to be noted that commercial product A is an emulsion in which oily components are emulsified with a hydrophilic nonionic surface active agent, commercial product B is the one whose main component is a linear alkyl quaternary ammonium salt.

| (Formulation) | | |
|---|---|---|
| (1) Mono-2-hexyldecyl phosphate L-arginine salt | 0.3% | |
| (2) Water | 1.4 | |
| (3) Glycerine | 3.89 | |
| (4) Oily ingredients* | 44.5 | |
| (5) Carboxy vinyl polymer | 0.1 | |
| (6) Sodium hydroxide (10% aq. sol'n) | 0.4 | |
| (7) Glycerine | 35 | |
| (8) Ethanol | balance | |
| *Oily ingredients: | Squalane | 24.5% |
| | Jojoba oil | 12 |
| | vaseline | 8 |

(Preparation)

Ingredients (1), (2) and (3) were mixed and homogenized by agitation at 60° C., and then ingredient (4) was added. Ingredients (5) to (8) preliminary mixed were added to the above mixture to obtain a body treatment composition of transparent gel.

12

(Results)

TABLE 5

| Evaluation Item** | Inventive Product | Commercial Product A | Commercial Product B |
|---|---|---|---|
| Affinity to the skin | 4 | 4 | 3 |
| Transparency | 5 | 3 | 1 |
| Remaining feel | 5 | 2 | 5 |
| Moistened feel | 4 | 3 | 3 |
| Less slimy sensation | 5 | 4 | 1 |

**The evaluation results were indicated by five steps. A higher numeral means a better evaluation.

EXAMPLE 11

Milky Emulsion:

A milky emulsion was prepared according to the following formulation.

| (Formulation) | |
|---|---|
| (1) Mono-2-octyllauryl phosphate L-arginine salt | 0.5% |
| (2) Glycerine aqueous solution (glycerine content = 86%) | 10.0 |
| (3) Octyldodecyl myristate | 20.0 |
| (4) Cholesteryl isostearate | 20.0 |
| (5) Purified water | 49.5 |

(Preparation)

Ingredients (1) and (2) were homogenized by agitation at 60° C. To the resultant gel, oily ingredients (3) and (4) were added and mixed to obtain a gel-like emulsion. Purified water (ingredient (5)) was added to the emulsion under agitation, thereby obtaining a milky emulsion.

What is claimed is:

1. A process for preparing a gel-like emulsion suitable for use in cosmetic and pharmaceutical applications, comprising adding an oil in an amount of 10 to 85 wt. % to a surfactant continuous phase, said surfactant continuous phase comprising 0.1 to 60% by weight of a monoalkyl phosphate salt of the following general formula (I), dissolved in an aqueous polyhydric alcohol solution, said aqueous polyhydric alcohol solution comprising not less than 60% by weight of a polyhydric alcohol and remainder water:

$$R-O-\underset{\underset{O}{\|}}{\overset{\overset{OH}{|}}{P}}-OX \qquad (I)$$

in which R represents a hydrocarbon group having from 12 to 24 carbon atoms and X represents an alkali metal, a basic amino acid or an organic base.

2. The process of claim 1, wherein R is a hydrocarbon group having from 12 to 18 carbon atoms.

3. The process of claim 1, wherein R is one member selected from the group consisting of linear alkyl groups, linear alkynyl groups and branched alkyl groups.

4. The process of claim 1, wherein R is a methyl-branched alkyl group of the formula:

$$CH_3-(CH_2)_h-CH(CH_3)-(CH_2)_i-$$

wherein h is an integer of from 2 to 14, i is an integer of from 3 to 11, and the sum of h+i is an integer of from 9 to 21, or R is a β-branched alkyl group of the formula:

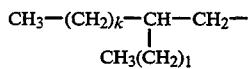

wherein k is an integer of from 5 to 11, l is an integer of from 3 to 10, and the sum of k+l is an integer of from 8 to 20.

5. The process of claim 1, wherein X is a salt of lithium, sodium, potassium, arginine, ornithine, lysine, oxylysine, triethanolamine, diethanolamine, or monoethanolamine.

6. The process of claim 1, wherein said polyhydric alcohol is at least one member selected from the group consisting of glycerine, ethylene glycol, diethylene glycol, triethylene glycol, hexanediol, butylene glycol, heptanediol, pentanediol, butanediol, propylene glycol, sorbitol, and maltitol.

7. The process of claim 1, wherein said oil is at least one member selected from the group consisting of hydrocarbons, esters of higher alcohols and higher fatty acids, higher alcohols, higher fatty acids, animal and plant oils and fats, cholesterol and fatty acid esters.

8. The process of claim 1, wherein said oil is at least one member selected from the group consisting of liquid paraffin, solid paraffin, vaseline (petrolatum), olive oil, squalene, hydrogenated coconut oil, jojoba oil, 2-ethylhexanoic acid triglyceride, octadecyl myristate, isostearyl cholesteryl ester, and silicone oil.

9. A process for preparing an O/W emulsion suitable for use in cosmetic and pharmaceutical applications, comprising adding an aqueous phase to a gel-like emulsion which is prepared by adding an oil in an amount of 10 to 85 wt % to a surfactant continuous phase, said surfactant continuous phase comprising 0.1 to 60% by weight of a monoalkyl phosphate salt of the following general formula (I), dissolved in an aqueous polyhydric alcohol solution, said aqueous polyhydric alcohol solution comprising not less than 60% by weight of a polyhydric alcohol and remainder water:

in which R represents a hydrocarbon group having from 12 to 24 carbon atoms and X represents an alkali metal, a basic amino acid or an organic base.

10. The process of claim 9, wherein R is a hydrocarbon group having from 12 to 18 carbon atoms.

11. The process of claim 9, wherein R is one member selected from the group consisting of linear alkyl groups, linear alkynyl groups and branched alkyl groups.

12. The process of claim 9, wherein R is a methyl-branched alkyl group of the formula:

wherein h is an integer of from 2 to 14, i is an integer of from 3 to 11, and the sum of h+i is an integer of from 9 to 21, or R is a β-branched alkyl group of the formula:

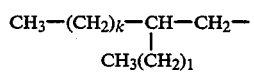

wherein k is an integer of from 5 to 11, l is an integer of from 3 to 10, and the sum of k+l is an integer of from 8 to 20.

13. The process of claim 9, wherein X is a salt of lithium, sodium, potassium, arginine, ornithine, lysine, oxylysine, triethanolamine, diethanolamine, or monoethanolamine.

14. The process of claim 9, wherein said polyhydric alcohol is at least one member selected from the group consisting of glycerine, ethylene glycol, diethylene glycol, triethylene glycol, hexanediol, butylene glycol, heptanediol, pentanediol, butanediol, propylene glycol, sorbitol, and maltitol.

15. The process of claim 9, wherein said oil is at least one member selected from the group consisting of hydrocarbons, esters of higher alcohols and higher fatty acids, higher alcohols, higher fatty acids, animal and plant oils and fats, cholesterol and fatty acid esters.

16. The process of claim 9, wherein said oil is at least one member selected from the group consisting of liquid paraffin, solid paraffin, vaseline (petrolatum), olive oil, squalene, hydrogenated coconut oil, jojoba oil, 2-ethylhexanoic acid triglyceride, octadecyl myristate, isostearyl cholesteryl ester, and silicone oil.

* * * * *